United States Patent [19]

Scherf

[11] 4,124,641

[45] Nov. 7, 1978

[54] OXYETHYLATED ACETALS

[75] Inventor: Gerhard W. H. Scherf, Dundas, Canada

[73] Assignee: Canadian D. A. Stuart Oil Co. Limited, Scarborough, Canada

[21] Appl. No.: 809,128

[22] Filed: Jun. 22, 1977

Related U.S. Application Data

[62] Division of Ser. No. 640,273, Dec. 12, 1975, abandoned.

[51] Int. Cl.$^2$ .................. C07C 43/30; C07D 295/08
[52] U.S. Cl. .................................... 568/601; 544/87; 544/177
[58] Field of Search .................................... 260/615 A

[56] References Cited

U.S. PATENT DOCUMENTS

| | | | |
|---|---|---|---|
| 2,397,514 | 4/1946 | Staff | 260/615 A |
| 2,885,443 | 5/1959 | Kress | 260/615 A |
| 2,905,719 | 9/1959 | de Benneville et al. | 260/615 A |
| 2,905,720 | 9/1959 | de Benneville et al. | 260/615 A |
| 2,905,721 | 9/1959 | de Benneville et al. | 260/615 A |

*Primary Examiner*—Jose Tovar
*Attorney, Agent, or Firm*—Neuman, Williams, Anderson & Olson

[57] ABSTRACT

A surface active compound comprises a lipophilic alkyl group linked to a hydrophilic oxyethylated group through an acetal linkage so that, on acidification of an aqueous medium containing such a surface active compound, rupture of such acetal linkage permits separation of said lipophilic alkyl group, possibly with lipid material associated therewith, from the aqueous medium in which the oxyethylated groups remain so in turn permitting recovery of such lipophilic groups and any such lipid material, and effective elimination of active surface active compound from the aqueous phase.

6 Claims, No Drawings

OXYETHYLATED ACETALS

This application is a continuation of application Ser. No. 640,273, filed December 12, 1975 and entitled "Enervatable Surface-Active Organic Compounds", now abandoned.

BACKGROUND OF THE INVENTION

The present invention relates to surface active compounds, their preparation and their use, and more particularly to surface active compounds which can have their structures readily modified to permit not only the separation and recovery of lipid material from an aqueous medium in which such compounds are used but also to provide, after such separation, an aqueous phase in which the contents of such lipid material and of active surface active material are substantially reduced.

A variety of surface active agents or compounds are well known and such compounds are used for a variety of purposes. Merely by way of example, there can be mentioned the uses of such compounds in household detergents and other cleaning compositions and in industrial products such as detergents, emulsifying agents, wetting agents, coupling agents and substantive agents as used in fabric treatment. Surface active compounds are generally used in aqueous media and it is fully recognized that the disposal of large quantities of waste waters containing surface active compounds presents numerous problems in sewage treatment plants and in natural bodies of water such as rivers and lakes into which such waste waters frequently find their way.

All surface active compounds have a molecular structure which comprises a lipophilic or hydrophobic portion or moiety bonded to a hydrophilic portion or moiety. It is believed that, in the use of a surface active compound in an aqueous medium, the hydrophilic portions of the molecules effectively become attached to water molecules so effectively providing dissolution of the compound in the aqueous medium. It is also believed that the lipophilic portions of such molecules become attached to any lipidic material which is present so as effectively to maintain that material in dispersion in the aqueous phase. For example, in the use of a household detergent, the lipophilic portions of the surface active compound molecules become associated with oil, grease or dirt molecules with the result that such molecules effectively become dissolved or at least dispersed in the aqueous phase. Since an excess of detergent will often be used, that aqueous phase will normally also contain molecules of the surface active compound with which no lipid molecules are associated. The principal problem which arises with such use of detergents is a result of the presence in the waste water of the surface active compound regardless of whether or not the molecules thereof have any lipid molecules associated therewith.

On the other hand, in the use, for example, of a surface active compound as an emulsifying agent to form an aqueous emulsion of an industrial cutting oil, the association with the molecules of the surface active compound of molecules of both water and the lipid material (i.e. the cutting oil) provides a stable emulsion which, if discarded after use into a waste water system, results not only in serious pollution of the waste water with both the surface active compound and the cutting oil but also to a significant loss of the valuable cutting oil itself.

Presently known surface active compounds fall, as is well known, into four classes, namely anionic, cationic, amphoteric and non-ionic which differ essentially in the manner in which their hydrophilic portions effectively associate with water molecules.

As hereinbefore indicated, the problems involved in the disposal of waste waters containing surface active compounds and lipid materials dispersed in such waters are fully recognized and attempts have heretofore been made to treat such waste waters to separate such surface active compounds and lipid materials from such waters. Some success has been attained in the purification of waste waters containing anionic and cationic surface active compounds by treating such waste waters with flocculating agents so as to rupture the so-called bonds between the hydrophilic moieties of the surface active compounds and the water molecules so as then to allow separation of a lipid phase and/or the surface active compound from the aqueous phase. Various adsorption processes have also been suggested for purifying waste waters containing surface active compounds and lipid materials. It has also been suggested to provide biodegradable surface active compounds which can be destroyed by certain bacteria.

The known processes for the deactivation and/or removal of surface active compounds from waste waters have, however, presented various problems. For example, the previously proposed adsorption processes are relatively slow and, for the treatment of large quantities of waste waters, call for substantial capital investment. Additionally, if it is then desired to recover the lipid material, it is then necessary to recover that material from the adsorbent at further expense.

Additionally, many of the previously proposed processes are not effective for deactivating non-ionic surface active compounds and consequently very substantial volumes of waste waters containing such compounds and lipid materials associated therewith are discarded each year into sewage plants and natural bodies of water. Additionally, the use of non-ionic surface active compounds is precluded in many applications in view of the difficulty of purifying waste waters containing such compounds.

It is a principal object of the present invention to provide a surface active compound which can readily be deactivated when present in waste waters so as then also to permit the ready removal from such waters of lipid material previously dispersed therein and to reduce the amount of active surface active compound which remains in the waste waters which are to be discarded.

It is a further object of this invention, in accordance with a preferred feature thereof, to provide an improved and de-activatable surface active compound.

Other objects of the invention will become apparent as the description herein proceeds.

SUMMARY OF THE INVENTION

A surface active compound in accordance with the present invention comprises, as do known surface active compounds, a molecular structure which comprises a lipophilic moiety or portion and chemically bonded so that lipophilic moiety a hydrophilic moiety. In distinction to known surface active compounds, those of the present invention include a bridging segment interconnecting the hydrophilic and lipophilic moieties and which incorporates a normally stable linkage which is, however, ruptured when such a surface active compound is exposed to a predetermined condition when dispersed in an aqueous medium. In the use of such surface active compounds under conditions other than such predetermined condition, the surface active compound functions in a normal manner. If, however, such a surface active compound present in an aqueous medium is subsequently exposed to such a predetermined condition, the rupture of the aforesaid linkage in the bridging segment permits separation of the lipophilic and hydrophilic moieties so as to provide two distinct phases. It will further be understood that, after such separation, the resulting aqueous phase will contain the hydrophilic moieties of the surface active compound while the lipidic phase will contain the lipophilic moieties of the surface active compound as well as any lipid material which was associated with those lipophilic moieties.

Although the present invention embraces many surface active compounds in which hydrophilic and lipophilic moieties are interconnected by a bridging segment incorporating a normally stable linkage which ruptures when such compound is exposed when dispersed in an aqueous medium to a predetermined condition, it has been found that surface active compounds having such a property can be manufactured at a reasonable cost if such normally stable linkage is one which ruptures when the surface active compound is dispersed in an aqueous medium at a pH value within a predetermined range of such values.

One particularly important group of surface active compounds in accordance with the present invention are acetals which correspond to the general formula:

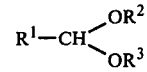

in which at least one of $R^1$, $R^2$ and $R^3$ represents a hydrophilic moiety and at least one of $R^1$, $R^2$ and $R^3$ represents a lipophilic moiety. These particular surface active compounds are structurally stable and function in the same manner as conventional surface active compounds when present in an aqueous medium at neutral or alkaline pH values. If, however, such an aqueous medium is acidified, the surface active compounds rupture in accordance with the following equation:

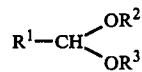 + $H_2O \Longrightarrow R^1$—CHO + $R^2OH$ + $R^3OH$

It will now be understood that, as a result of the acidification of the aqueous medium in which such a surface active compound is dispersed, that compound breaks down into separate hydrophilic and lipophilic components.

While one of the group $R^1$, $R^2$ and $R^3$ must be a lipophilic one and while one of these groups must be a hydrophilic one, so that the complete compound will normally present surface active properties, the third one of those groups $R^1$, $R^2$ and $R^3$ can be lipophilic or hydrophilic or it can be relatively inert in that it presents no marked lipophilic or hydrophilic property.

Another possibility within the scope of this invention is to provide a surface active compound corresponding to the aforementioned general formula:

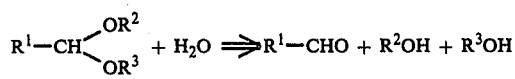

and in which one of the groups $R^1$, $R^2$ and $R^3$ is hydrophilic, in which one of those groups is lipophilic and in which the third one of the groups $R^1$, $R^2$ and $R^3$ comprises a further hydrophilic segment bonded to a further lipophilic segment through a further acetal linkage.

Examples of such a class of compounds are those which correspond to the formula:

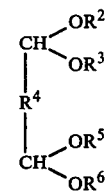

in which at least one of $R^2$, $R^3$, $R^4$, $R^5$ and $R^6$ represents a hydrophilic moiety and in which at least one of $R^2$, $R^3$, $R^4$, $R^5$ and $R^6$ represents a lipophilic moiety.

Although this invention is not restricted to surface active compounds in which the lipophilic and hydrophilic moieties are of any particular structure, there may be mentioned merely for the sake of illustrating this invention particular structures for such moieties which have in practice proven to be highly effective. For example, the lipophilic moieties in surface active compounds in accordance with this invention are usefully straight and branched chain hydrocarbon groups having from 8 to 24 carbon atoms and more usually from 10 to 18 carbon atoms. Typical of such groups are stearyl and myristyl groups. Other especially suitable lipophilic moieties are alkylated aromatic groups particularly those having from 6 to 18 carbon atoms in their alkyl group.

Typical hydrophilic moieties for use in non-ionic surface active compounds in accordance with the present invention are hydrophilic oxyalkylated groups and especially oxyethylated groups containing from 1 to 24 oxyethylene groups. Typical preferred hydrophilic groups are as follows:

--- a. oxyethylated methyl groups
   —$(C_2H_4O)_{3-6}CH_3$ b. oxyethylated n-butyl groups
   —$(C_2H_4O)_{1-12}(CH_2)_3CH_3$ c. oxyethylated N-morpholine groups $$-(C_2H_4O)_{3-6}-N\begin{matrix}CH_2-CH_2\\ \\ CH_2\quad CH_2\end{matrix}O$$

---

The surface active compounds of this invention can be prepared by any appropriate procedure. Those containing one or more acetal groups and corresponding to the formula:

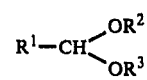

in which $R^1$, $R^2$ and $R^3$ are as previously defined are usefully prepared in accordance with another feature of this invention by the condensation of an aldehyde with an alcohol in accordance with the following equation:

$$R^1CHO + R^2OH + R^3OH \Rightarrow R^1-CH\begin{matrix}OR^2\\OR^3\end{matrix} + H_2O$$

Such a condensation reaction can be carried out in the presence of an acidic catalyst at an elevated temperature and in a suitable solvent such as benzene to permit separation of the water by azeotropic distillation. After completion of the condensation reaction, the acid catalyst will be neutralized so that the products can be used in aqueous media without undesired rupture of the acetal linkage until such time as it is desired to cause such rupture to occur.

For example, in such a preparation, a hydrophilic aldehyde can be condensed with one or more lipophilic alcohols or a lipophilic aldehyde can be condensed with one or more hydrophilic alcohols.

It is also within the scope of this invention to condense an aldehyde with both a hydrophilic alcohol and a lipophilic alcohol. In such a process, the aldehyde itself may be either lipophilic or hydrophilic or may be one which presents no marked hydrophilic or lipophilic property. Such a condensation can be represented by the following equations:

$$R^1CHO + \begin{matrix}HOR^7\\HOR^8\end{matrix} \Rightarrow R^1CH\begin{matrix}OR^7\\OR^8\end{matrix} + H_2O \quad \text{I}$$

$$R^1CHO + \begin{matrix}HOR^7\\HOR^7\end{matrix} \Rightarrow R^1CH\begin{matrix}OR^7\\OR^7\end{matrix} + H_2O \quad \text{II}$$

$$R^1CHO + \begin{matrix}HOR^8\\HOR^8\end{matrix} \Rightarrow R^1CH\begin{matrix}OR^8\\OR^8\end{matrix} + H_2O \quad \text{III}$$

If $R^1$ represents a group which has no marked hydrophilic or lipophilic property and if $R^7$ and $R^8$ respectively represent groups having marked lipophilic and hydrophilic properties, it will be understood that there will generally be obtained a mixture of the products I, II and III having different properties, namely the surface active product I including both a hydrophilic moiety and a lipophilic moiety interconnected through a rupturable acetal linkage, the essentially totally lipophilic product II and the essentially totally hydrophilic product III.

For some applications and with some reactant materials, the resulting product mixture can be used as such whereas, in other circumstances, it will be desirable to separate the desired product, such as product I, from the product mixture. With other starting materials, it will be possible to control the condensation reaction conditions to favour the production of the desired mixed hydrophilic/lipophilic product.

Other features of the invention and the advantages presented thereby will become apparent as the description herein proceeds.

The invention will now be further described by way of illustration in the following Examples:

EXAMPLE 1

Stearyl aldehyde in the amount of 26.8 gm was mixed with 60 gm of a water-soluble oxyethylated alcohol obtained by treating methanol with six molecules of ethylene oxide. The pH value of the resulting liquid mixture was then adjusted to a value of 3.0 by the dropwise addition of concentrated hydrochloric acid and the mixture was then heated for 1 hour with continuous agitation at a temperature of 70°-75° C. To the reaction mixture, there were then added 50 ml benzene and the water formed during the acetal formation reaction was removed by azeotropic distillation. After 8 gm of water had been removed, the reaction mixture was cooled to room temperature and was then carefully adjusted to a pH of 9.5 - 10.5 by the dropwise addition of a 50% aqueous solution of sodium hydroxide. The benzene solvent was then removed by evaporation under a reduced pressure of 10-20 mm Hg at 70° C, adding occasionally during the evaporation process small amounts of an aqueous solution of sodium hydroxide to maintain alkalinity. The final product was a viscous yellowish liquid.

The reaction is shown in the following equation:

$$CH_3(CH_2)_{16}CHO + 2HO(C_2H_4O)_6CH_3 \Rightarrow$$
$$CH_3(CH_2)_{16}CH\begin{matrix}O(C_2H_4O)_6CH_3\\O(C_2H_4O)_6CH_3\end{matrix} + H_2O$$

A 1% aqueous solution of the product formed a stable foam when shaken. Upon adjusting the pH value of this solution to 3.0 by the addition of hydrochloric acid, the foam disappeared and could not be regenerated by mechanical agitation.

A 10% aqueous solution of the product exhibited a surface tension of 45.0 dynes/cm at a pH of 11.8. After the addition of 4.5 ml of 10% hydrochloric acid to 20 ml of that 10% aqueous solution, the surface tension of the resulting mixture increased to a value of 55.2 dynes/cm at the prevailing pH of 3.8.

EXAMPLE 2

Stearyl aldehyde in the amount of 13.4 gm was mixed with 62.0 gm of a water-soluble oxyethylated alcohol obtained by treating n-butanol with twelve molecules of ethylene oxide. The pH value of the resulting liquid mixture was then adjusted to a value of 3.0 by the dropwise addition of concentrated hydrochloric acid and the mixture was then heated for 1 hour with continuous agitation at a temperature of 70°-75° C. To the reaction mixture, there were then added 50 ml of benzene and the water formed during the acetal formation reaction was removed by azeotropic distillation. After 8 gm of water had been removed, the reaction mixture was cooled to room temperature and was then carefully adjusted to a pH of 9.5 - 10.5 by the dropwise addition of a 50% aqueous solution of sodium hydroxide. The benzene solvent was then removed by evaporation under a reduced pressure of 10-20 mm Hg at 70° C, adding occasionally during the evaporation process small amounts of an aqueous solution of sodium hydroxide to maintain alkalinity. The final product was a viscous yellowish liquid.

The reaction is shown in the following equation:

$$CH_3(CH_2)_{16}CHO + 2HO(C_2H_4O)_{12}C_4H_9 \Rightarrow$$
$$CH_3(CH_2)_{16}CH\begin{matrix}O(C_2H_4O)_{12}C_4H_9\\O(C_2H_4O)_{12}C_4H_9\end{matrix} + H_2O$$

A 1% aqueous solution of the product formed a stable foam when shaken. Upon adjusting the pH value of this solution to 3.0 by the addition of hydrochloric acid, the foam disappeared and could not be regenerated by mechanical agitation.

A 10% aqueous solution of the product exhibited a surface tension of 41.2 dynes/cm at a pH of 12.6. After the addition of 14.5 ml of 10% hydrochloric acid to 20 ml of that 10% aqueous solution, the surface tension of the resulting mixture increased to a value of 54.0 dynes/cm at the prevailing pH of 3.8.

EXAMPLE 3

Stearyl aldehyde in the amount of 26.8 gm was mixed with 33.0 gm of a water-soluble oxyethylated alcohol obtained by treating methanol with three molecules of ethylene oxide. The pH value of the resulting liquid mixture was then adjusted to a value of 3.0 by the dropwise addition of concentrated hydrochloric acid and the mixture was then heated for 1 hour with continuous agitation at a temperature of 70°–75° C. To the reaction mixture, there were then added 50 ml of benzene and the water formed during the acetal formation reaction was removed by azeotropic distillation. After 8 gm of water had been removed, the reaction mixture was cooled to room temperature and was then carefully adjusted to a pH of 9.5 – 10.5 by the dropwise addition of a 50% aqueous solution of sodium hydroxide. The benzene solvent was then removed by evaporation under a reduced pressure of 10–20 mm of Hg at 70° C, adding occasionally during the evaporation process small amounts of an aqueous solution of sodium hydroxide to maintain alkalinity. The final product was a viscous yellowish liquid.

The reaction is shown in the following equation:

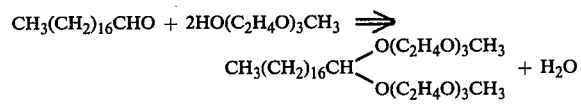

A 1% aqueous solution of the product formed a stable foam when shaken. Upon adjusting the pH value of this solution to 3.0 by the addition of hydrochloric acid, the foam disappeared and could not be regenerated by mechanical agitation.

A 10% aqueous solution of the product exhibited a surface tension of 29.5 dynes/cm at a pH of 11.8. After the addition of 5.0 ml of 10% hydrochloric acid to 20 ml of that 10% aqueous solution, the surface tension of the resulting mixture increased to a value of 49.2 dynes/cm at the prevailing pH of 3.8.

EXAMPLE 4

Stearyl aldehyde in the amount of 13.4 gm was mixed with 53 gm of a water-soluble oxyethylated derivative of morpholine obtained by treating that substance with ethylene oxide to obtain a mixture of products containing from 3 to 6 and averaging about 4.5 moles of ethylene oxide per molecule. The pH value of the resulting liquid mixture was then adjusted to a value of 3.0 by the dropwise addition of concentrated hydrochloric acid and the mixture was then heated for 1 hour with continuous agitation at a temperature of 70°–75° C. To the reaction mixture, there were then added 50 ml of benzene and the water formed during the acetal formation reaction was removed by azeotropic distillation. After 8 gm of water had been removed, the reaction mixture was cooled to room temperature and was then carefully adjusted to a pH of 9.5 – 10.5 by the dropwise addition of a 50% aqueous solution of sodium hydroxide. The benzene solvent was then removed by evaporation under a reduced pressure of 10–20 mm Hg at 70° C, adding occasionally during the evaporation process small amounts of an aqueous solution of sodium hydroxide to maintain alkalinity. The final product was viscous yellowish liquid.

The reaction is shown in the following equation:

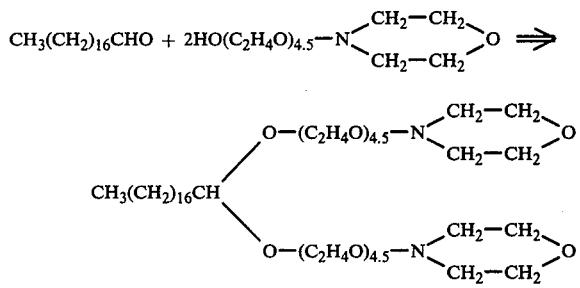

A 1% aqueous solution of the product formed a stable foam when shaken. Upon adjusting the pH value of this solution to 3.0 by the addition of hydrochloric acid, the foam disappeared and could not be regenerated by mechanical agitation.

A 10% aqueous solution of the product exhibited a surface tension of 31.1 dynes/cm at a pH of 12.0. After the addition of 8.5 ml of 10% hydrochloric acid to 20 ml of that 10% aqueous solution, the surface tension of the resulting mixture increased to a value of 50.4 dynes/cm at the prevailing pH of 3.8.

EXAMPLE 5

Myristyl aldehyde in the amount of 21.2 gm was mixed with 26.0 gm of butylcellosolve (glycol monobutyl ether) having the formula: $C_4H_9OC_2H_4OH$. The pH value of the resulting liquid mixture was then adjusted to a value of 3.0 by the dropwise addition of concentrated hydrochloric acid and the mixture was then heated for 1 hour with continuous agitation at a temperature of 70°–75° C. To the reaction mixture, there were then added 50 ml of benzene and the water formed during the acetal formation reaction was removed by azeotropic distillation. After 8 gm of water had been removed, the reaction mixture was cooled to room temperature and was then carefully adjusted to a pH of 9.5 – 10.5 by the dropwise addition of 50% aqueous solution of sodium hydroxide. The benzene solvent was then removed by evaporation under a reduced pressure of 10–20 mm Hg at 70° C, adding occasionally during the evaporation process small amounts of an aqueous solution of sodium hydroxide to maintain alkalinity. The final product was a viscous yellowish liquid.

The reaction is shown in the following equation:

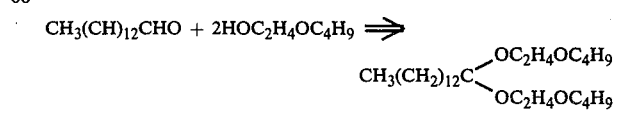

A 1% aqueous solution of the product formed a stable foam when shaken. Upon adjusting the pH value of this solution to 3.0 by the addition of hydrochloric acid, the foam disappeared and could not be regenerated by mechanical agitation.

A 10% aqueous solution of the product exhibited a surface tension of 30.0 dynes/cm at a pH of 11.0. After the addition of 5.2 ml of 10% hydrochloric acid to 20 ml of that 10% aqueous solution, the surface tension of the resulting mixture increased to a value of 38.0 dynes/cm at the prevailing pH of 3.8.

EXAMPLE 6

Stearyl alcohol in the amount of 27.0 gms was mixed with 5.8 gm of glyoxal and 89 gm of a water-soluble oxyethylated alcohol obtained by treating methanol with six moles of ethylene oxide. The pH value of the resulting liquid mixture was then adjusted to a value of 3.0 by the dropwise addition of concentrated hydrochloric acid and the mixture was subsequently heated for 1 hour with continuous agitation at a temperature of 70°-75° C. To the reaction mixture, there were then added 50 ml benzene and the water formed during the acetal formation reaction was removed by azeotropic distillation. After 14 gm of water had been removed, the reaction mixture was cooled to room temperature and was then carefully adjusted to a pH of 9.5 – 10.5 by the dropwise addition of a 50% aqueous solution of sodium hydroxide. The benzene solvent was then removed by evaporation under a reduced pressure of 10-20 mm Hg at 70° C, adding occasionally during the evaporation process small amounts of an aqueous solution of sodium hydroxide to maintain alkalinity. The final product was a viscous yellowish liquid.

It is believed that the following reactions take place:

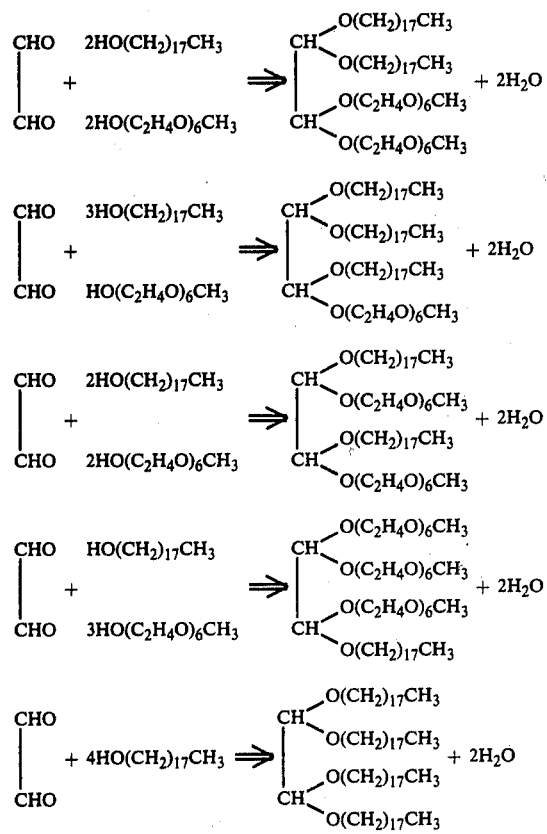

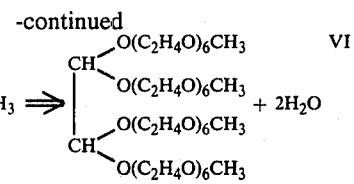

Of the products obtained, those indicated at I, II, III and IV present the desired surface active property while the products indicated at V and VI are not significantly surface active. The product mixture obtained did, however, show the desirable properties provided in accordance with this invention as will be understood by observation of the test results set down below.

A 1% aqueous solution of the mixed product formed a stable foam when shaken. Upon adjusting the pH value of this solution to 3.0 by the addition of hydrochloric acid, the foam disappeared and could not be regenerated by mechanical agitation.

A 10% aqueous solution of the product mixture exhibited a surface tension of 31.5 dynes/cm at a pH of 11.0. After the addition of 4.3 ml of 10% hydrochloric acid to 20 ml of that 10% aqueous solution, the surface tension of the resulting mixture increased to a value of 47.2 dynes/cm at the prevailing pH of 3.8.

EXAMPLE 7

Stearyl alcohol in the amount of 27.0 gm was mixed with 5.8 gm of glyoxal and 49.2 gm of a water-soluble oxyethylated alcohol obtained by treating methanol with three moles of ethylene oxide. The pH value of the resulting liquid mixture was then adjusted to a value of 3.0 by the dropwise addition of concentrated hydrochloric acid and the mixture was then heated for 1 hour with continuous agitation at a temperature of 70°-75° C. To the reaction mixture, there were then added 50 ml of benzene and the water formed during the acetal formation reaction was removed by azeotropic distillation. After 14 gm of water had been removed, the reaction mixture was cooled to room temperature and was then carefully adjusted to a pH of 9.5 – 10.5 by the dropwise addition of 50% aqueous solution of sodium hydroxide. The benzene solvent was then removed by evaporation under a reduced pressure of 10-20 mm at 70° C, adding occasionally during the evaporation process small amounts of an aqueous solution of sodium hydroxide to maintain alkalinity. The final product was a viscous yellowish liquid.

It is believed that a mixture of products is obtained as was the case in Example 6. The product mixture which was obtained presented the properties indicated below.

A 1% aqueous solution of the mixed product formed a stable foam when shaken. Upon adjusting the pH value of this solution to 3.0 by the addition of hydrochloric acid, the foam disappeared and could not be regenerated by mechanical agitation.

A 10% aqueous solution of the product mixture exhibited a surface tension of 34.6 dynes/cm at a pH of 11.0. After the addition of 2.7 ml of 10% hydrochloric acid to 20 ml of that 10% aqueous solution, the surface tension of the resulting mixture increased to a value of 48.2 dynes/cm at the prevailing pH of 3.8.

EXAMPLE 8

Terephthaldehyde in the amount of 13.4 gm was mixed with 27.0 gm of stearyl alcohol and 116 gm of a water-soluble oxyethylated derivative of morpholine obtained by treating that substance with ethylene oxide to obtain a mixture of products containing from 3 to 6 and averaging about 4.5 moles of ethylene oxide per molecule. The pH value of the resulting liquid mixture was then adjusted to a value of 3.0 by the dropwise addition of concentrated hydrochloric acid and the mixture was then heated for 1 hour with continuous agitation at a temperature of 70°–75° C. To the reaction mixture, there were then added 50 ml of benzene and the water formed during the acetal formation reaction was removed by azeotropic distillation. After 8 gm of water had been removed, the reaction mixture was cooled to room temperature and was then carefully adjusted to a pH of 9.5 – 10.5 by the dropwise addition of a 50% aqueous solution of sodium hydroxide. The benzene solvent was then removed by evaporation under a reduced pressure of 10 – 20 mm Hg at 70° C, adding occasionally during the evaporation process, small amounts of an aqueous solution of sodium hydroxide to maintain alkalinity. The final product was a viscous reddish liquid.

As was the case is Examples 6 and 7, it is believed that a mixture of reaction products is obtained, one of which will correspond to the following formula:

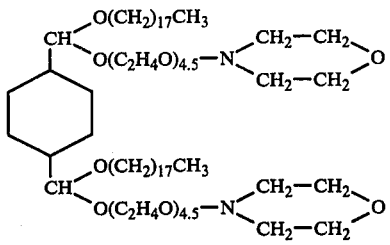

A 1% aqueous solution of the mixed product formed a stable foam when shaken. Upon adjusting the pH value of this solution to 3.0 by the addition of hydrochloric acid, the foam disappeared and could not be regenerated by mechanical agitation.

A 10% aqueous solution of the product mixture exhibited a surface tension of 52.0 dynes/cm at a pH of 10.5. After the addition of 3.2 ml of 10% hydrochloric acid to 20 ml of that 10% aqueous solution, the surface tension of the resulting mixture increased to a value of 57.8 dynes/cm at the prevailing pH of 3.8.

EXAMPLE 9

Dodecanol in the amount of 18.6 gm was mixed with 5.8 gm of glyoxal and 49.2 gm of a water-soluble oxyethylated alcohol obtained by treating methanol with three moles of ethylene oxide per molecule. The pH value of the resulting liquid mixture was then adjusted to a value of 3.0 by the dropwise addition of concentrated hydrochloric acid and the mixture was then heated for 1 hour with continuous agitation at a temperature of 70°–75° C. To the reaction mixture, there were then added 50 ml of benzene and the water formed during the acetal formation reaction was removed by azeotropic distillation. After 14 gm of water had been removed, the reaction mixture was cooled to room temperature and was then carefully adjusted to a pH of 9.5 – 10.5 by the dropwise addition of a 50% aqueous solution of sodium hydroxide. The benzene solvent was then removed by evaporation under a reduced pressure of 10 – 20 mm Hg at 70° C, adding occasionally, during the evaporation process, small amounts of an aqueous solution of sodium hydroxide to maintain alkalinity. The final product was a viscous reddish liquid.

It is believed that a mixture of products is obtained as in several of the preceeding Examples; one of those products will have the formula:

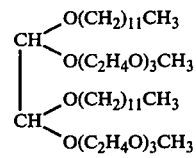

A 1% aqueous solution of the mixed product formed a stable foam when shaken. Upon adjusting the pH value of this solution to 3.0 by the addition of hydrochloric acid, the foam disappeared and could not be regenerated by mechanical agitation.

A 10% aqueous solution of the product mixture exhibited a surface tension of 27.2 dynes/cm at a pH of 11.0. After the addition of 3.2 ml of 10% hydrochloric acid to 20 ml of that 10% aqueous solution, the surface tension of the resulting mixture increased to a value of 48.0 dynes/cm at the prevailing pH of 3.8.

EXAMPLE 10

An emulsion base was prepared by blending the following materials:

| | |
|---|---|
| Acetal prepared as described in Example 7 | 7.6 g |
| Potassium hydroxide | 1.5 g |
| Water | 0.6 g |
| Hexylene glycol | 1.0 g |
| "Sun Oil - 100 seconds"* | 5.6 g |

*An oil conventionally used in the manufacture of cutting oil emulsions.

5 g of the emulsion base were then blended with 1 g of hexylene glycol and a further 5 g of Sun Oil - 100 seconds and the resulting blend was emulsified in 190 g of water.

On the addition of 10 ml concentrated hydrochloric acid to the emulsion, that emulsion immediately broke down and separated during a period of about 20 minutes into two clearly defined layers — an upper oily layer and an aqueous lower layer.

EXAMPLE 11

One ounce of the acetal prepared as described in Example 1 was used together with 0.5 ounces of sodium carbonate in a conventional household electric dishwasher having a single washing cycle of 10 minutes. The first discharge of waste water was collected and it was noted that the dirt and grease were fully dispersed in that waste water.

After acidification of that waste water with 10 ml of concentrated sulphuric acid, the suspended grease and solid particles separated and floated on the surface of the treated waste water.

After two further rinsing cycles, the dishes appeared as clean as when a conventional detergent was used.

What is claimed is:

1. A surface active acetal compound having the formula:

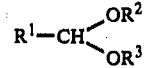

wherein at least one of $R^1$, $R^2$ and $R^3$ is an unsubstituted lipophylic alkyl group having from 8 to 24 carbon atoms and at least one of $R^1$, $R^2$ and $R^3$ is a hydrophylic oxyethylated group having the formula $-(C_2H_4O)-_n$ wherein $n$ is an integer of from 1 to 24 bonded to an unsubstituted terminal alkyl group of from 1 to 4 carbon atoms, and wherein $R^1$, $R^2$ and $R^3$ are selected from the group consisting of said unsubstituted lipophylic alkyl group and said hydrophylic oxyethylated group.

2. A surface active compound as claimed in claim 1 and in which, in said formula, $R^1$ represents an unsubstituted lipophylic alkyl group having from 10 to 18 carbon atoms.

3. A surface active compound as claimed in claim 2 and which corresponds to the formula:

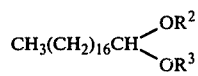

4. A surface active compound as claimed in claim 3 and which corresponds to the formula:

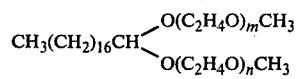

in which $m$ and $n$ represent integers from 3 to 6.

5. A surface active compound as claimed in claim 3 and which corresponds to the formula:

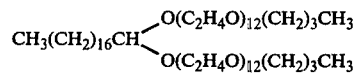

6. A surface active compound as claimed in claim 3 and which corresponds to the formula:

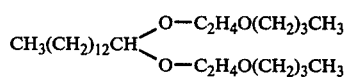

* * * * *